United States Patent [19]

DuFault

[11] Patent Number: 4,793,361
[45] Date of Patent: Dec. 27, 1988

[54] DUAL CHANNEL P-WAVE DETECTION IN SURFACE ELECTROCARDIOGRAPHS

[75] Inventor: Robert A. DuFault, Roseville, Minn.

[73] Assignee: Cardiac Pacemakers, Inc., St. Paul, Minn.

[21] Appl. No.: 25,731

[22] Filed: Mar. 13, 1987

[51] Int. Cl.$^4$ .................................................. A61B 5/04
[52] U.S. Cl. ................................................... 128/696
[58] Field of Search .......... 128/696, 704, 705, 419 PG

[56] References Cited

U.S. PATENT DOCUMENTS

| 4,537,200 | 8/1985 | Widrow | 128/696 |
| 4,543,963 | 10/1985 | Gessman | 128/419 PG |
| 4,557,266 | 12/1985 | Schober | 128/419 PG |

Primary Examiner—Francis J. Jaworski
Assistant Examiner—George Manuel
Attorney, Agent, or Firm—Orrin M. Haugen; Thomas J. Nikolai; Frederick W. Niebuhr

[57] ABSTRACT

A method and apparatus for reliably detecting the P-wave component in a surface electrocardiograph. An adaptive Least Means Square filter is implemented in a programmed computer and the computer receives as its inputs a digitized version of the ECG waves picked up from two discrete locations on a subject's chest wall. The LMS adaptive filter functions to accommodate the energy component of the QRS complex thereby leaving the P-wave as the paramount signal component in the filter's "error" output.

5 Claims, 2 Drawing Sheets

DUAL CHANNEL P-WAVE DETECTION IN SURFACE ELECTROCARDIOGRAPHS

BACKGROUND OF THE INVENTION

I. Field of the Invention

This invention relates generally to biomedical monitoring apparatus, and more particularly to a non-invasive system for segregating P-wave activity from a surface electrocardiograph.

II. Background of the Invention

Automatic analysis of supraventricular arrhythmias in a surface electrocardiogram (ECG) is hampered by the difficulty of detecting P-waves reliably. Because of the relatively poor signal-to-noise ratio between P-waves and other overriding electrical activity picked up by the surface electrodes and because there is a spectral overlap between the P-waves and the QRS complex, traditional linear filtering and thresholding techniques cannot be relied upon to provide the degree of discrimination necessary to uniquely identify a ECG component as a P-wave. In a publication entitled "Automatic Tachycardia Recognition", PACE 7: Part II, 541-547, May-June 1984, Dr. Arzbaecher reported on the use of an esophageal lead including a pickup device suspended from fine wires that is swallowed so as to position the sensor in desired proximity to the heart for enhancing the detection of the P-wave apart from the QRS complex. Detection or recording apparatus is connected to leads exiting the patient's mouth. The enhanced ability to monitor supra-ventricular arrhythmias offered by this and other invasive and semi-invasive approaches emphasizes the need for a non-invasive approach for use in situations where other techniques are not clinically appropriate. It is thus the main object of the present invention to provide a non-invasive means for detecting P-waves in signals obtained from surface ECG electrodes in a reliable fashion.

In accordance with the present invention, an adaptive filter of the type described in "Adaptive Signal Processing" by B. Widrow and S. Stearns, Prentice-Hall, Inc., N.J., copyright 1985, and referred as the Least Mean Square algorithm, is used to suppress the energy of the QRS complex in surface electrocardiograms to thereby render the P-wave more detectable in the resulting processed waveform. (Terminology such as "estimate", "error" and "desired" signals follow conventions set forth in this reference.) In the Widrow et al publication, the LMS adaptive filter technique is used as a noise canceller. Described is a scheme in which one signal, containing superimposed noise, is applied to a first channel while another signal, containing the noise alone in a form linearly related to the noise in the first channel, is applied to the second channel of the so-called "LMS filter". This filter is made to continuously adapt, ultimately converging so as to furnish an "estimate" of the noise received on the first channel. This "estimate" is subtracted from the composite signal and noise arriving on the first channel, resulting in an "error" signal which approximates the noise-free signal.

In our co-pending application filed concurrently herewith and entitled "DUAL CHANNEL COHERENT FIBRILLATION DETECTION SYSTEM", Ser. No. 025,811 the content of which is hereby incorporated by reference, there is described another application of the LMS algorithm and in that application the method of implementing the algorithm using a digital computer is set out. That application also defines various terms and parameters, again following Widrow and Stearns, which are also used herein.

In applying the LMS adaptive filter algorithm to the detection of P-waves in surface ECG waveforms, a pair of standard ECG leads positioned on the chest wall each pick up signals which respectively become the "input" and the "dresired" operands for the LMS filter. Each channel is driven by the cardiac atrial and ventricular equivalent dipoles which, in turn, comprise linear summations of cellular action potential sequences. To achieve ideal performance in suppressing the QRS component from a surface ECG lead, the surface lead should be the "desired" signal, while an independent source of the QRS signal should be used as the "input". Ideally, the "input" should derive from an endocardial ventricular catheter, since such a signal would be entirely free of the P-wave. This application differs in that both the "input" and "desired" channels contain both P-waves and QRS waves. However, by using two chest unipolar leads, such as V1 and V5, the QRS contains much more energy than the P-wave. Furthermore, the QRS morphology changes from uniphasic to biphasic to negative-uniphasic across the chest leads, while the P-wave exhibits approximately constant morphology in the same leads. By judiciously selecting the number of tap weights for the finite impulse response filter, it can be made to accommodate one but not both of the QRS complex and the P-wave. Because of the significant energy differential between the QRS complex and a P-wave, the QRS complex will have a predominant effect on the weight vector, and hence, the LMS filter will adapt primarily to the QRS complex. The phase difference which the filter must generate to cancel the QRS will also be applied to the P-wave. Subtracting the "estimate" from the "desired" now produces an "error" signal in which the QRS is effectively cancelled, while the P-wave, subjected to the same transformation, does not cancel and may even be augmented. Thus, the P/QRS energy ratio now favors P-wave detection, which may be accomplished by ordinary filtering and thresholding techniques.

OBJECTS

It is accordingly a principal object of the present invention to provide a new and improved method and apparatus for detecting P-waves in surface electrocardiograms.

Another object of the invention is to provide an adaptive filter for effectively nulling the QRS energy in a surface electrocardiogram leaving the P-wave energy substantially unattenuated.

Yet another object of the invention is to provide an apparatus including an adaptive filter configured in accordance with the LMS algorithm and connected to a pair of surface ECG electrodes configured such that the P/QRS energy ratio is enhanced.

These and other objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
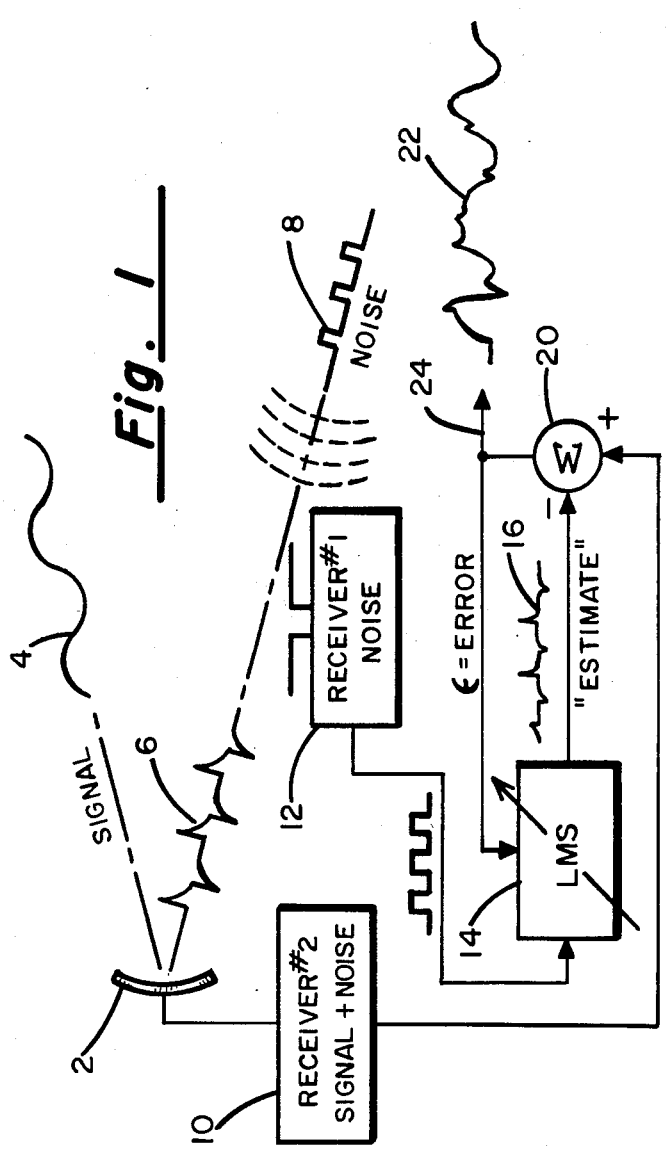
FIG. 1 is a schematic diagram useful in explaining the operation of the LMS algorithm.

To gain a clearer understanding of the LMS process, it is believed expedient to illustrate its operation in a typical noise canceller application and, in this regard, reference is made to the block diagram of FIG. 1. An antenna 2 is illustrated as receiving simultaneously an information signal 4 and an additive noise component 6 which is typically altered in an unknown fashion between the noise source 8 and the output of receiver no. 2 which is identified by numeral 10. At this point, it is not known which portion of the received signal is due to the superimposed noise. If an independent source of the noise is available as at the output of receiver no. 1, identified by numeral 12, that source may be used as the "input" to the LMS adaptive filter 14. The transfer function of the LMS filter continuously adapts to furnish an "estimate" of the noise as registered at receiver 2. The wave 16 is intended to illustrate the adaptation as time progresses. The noise-laden signal emanating from receiver no. 2 is represented by the waveform 18 and is applied as an input to a subtracter 20. The second input to this subtracter is the "estimate" wave 16 and the resultant signal 22 appears on the "error" output line 24. This "error" signal is fed back to the LMS adaptive filter 14 and is used to adjust the weight parameters thereof until the "error" and the "input" signals are mutually uncorrelated and incoherent. At this point, the "error" signal then approximates the noise-free signal segments of the wave 22.

Figure 2:
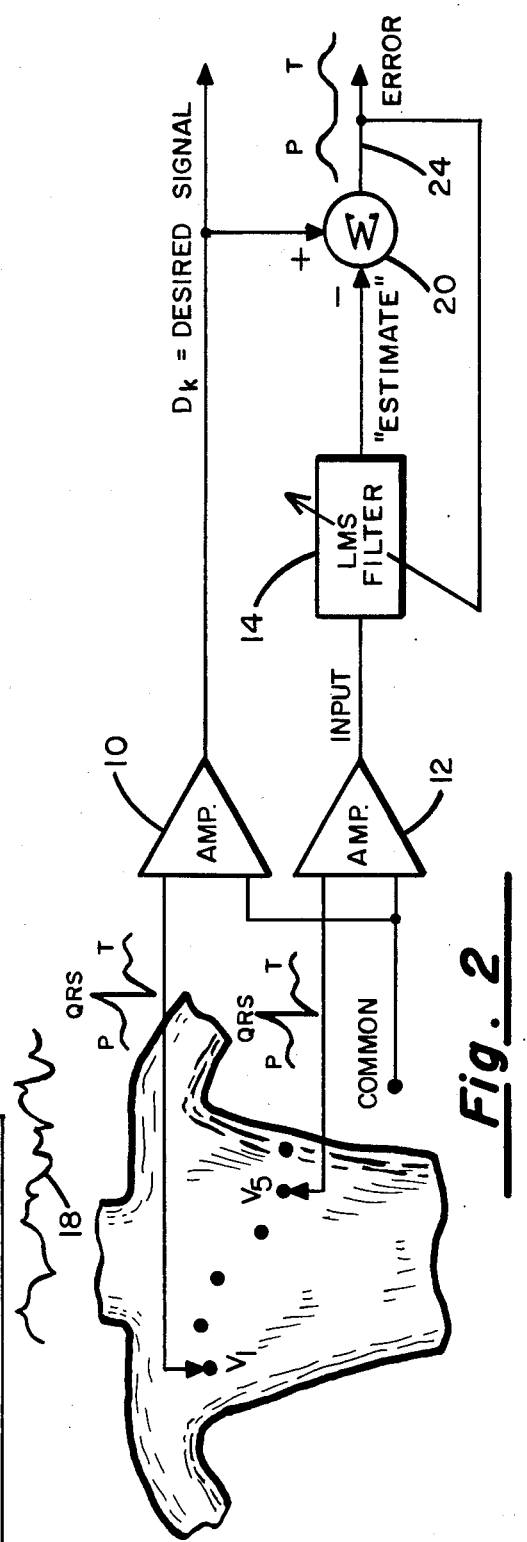
FIG. 2 is a block diagram showing the way of applying the LMS adaptive filter to a pair of ECG leads.

In applying the LMS algorithm to the detection of P-waves in surface electrocardiograms, it is necessary that there be two distinct surface ECG channels such that one channel can be considered as the source of the signal observed on the other. The atria and the ventricles, acting as independent generators, transmit their respective signals to the chest wall. As shown in FIG. 2, leads $V_1$ and $V_5$ are selected to provide the "input" and the "desired" operands to the LMS filter. As mentioned above, both channels, $V_1$ and $V_5$ are driven by the cardiac atrial and ventricle equivalent dipoles which comprise linear summations of cellular action potential sequences, and, therefore, each contains both P and QRS energy. Ideally, one would like to have an independent source of the interfering QRS signal, such as might be obtained using a ventricular catheter, but in practice, any two non-invasive surface ECG leads will suffice, providing there is a significant algebraic or vector difference in the P-wave versus the QRS wave between the two leads. Thus, for example, if A/V disassociation exists or if there are significant differences in the P/QRS amplitude ratios or if significant differences in the P and the QRS phase properties prevail, then two surface contacting electrodes, containing the PQRST complex in contrasting form, can be used.

As is set out in my aforereferenced co-pending application, the LMS algorithm operates to cancel any energy which is coherent between the "input" signal and the "desired" signal, i.e., the signals picked up by surface electrodes $V_5$ and $V_1$, respectively. Thus, any energy that is related by a linear transform between the two leads in question tends to be cancelled. When it is considered that the QRS complex represents a significantly greater amount of energy than does the P-wave, the adjustment of the tap weights of the LMS adaptive filter is dominated by the QRS complex in just the ratio of QRS energy to P and T wave energy. The QRS complex is thus accommodated (cancelled). With the QRS energy substantially eliminated, the P-wave achieves greater prominence in the residue and, is therefore, more detectable. Due to artifacts attributable to movement of the heart beneath the ribcage or motion of the electrodes on the surface of the body, a residual level of noise remains in the "error" output from the summing device 20. This residual noise adds to the background noise against which the P-wave must be disconnected. However, by applying bandpass filtering to the error channel, further enhancement of the P-wave energy results.

Figure 3:
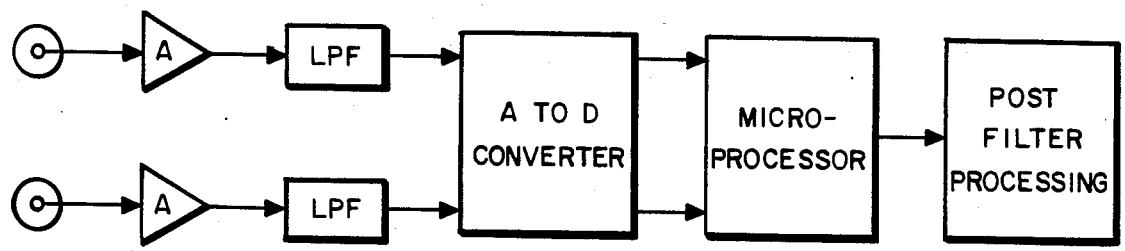
FIG. 3 is a block diagram of a digital computer implementation of the present invention.

Referring to FIGS. 2 and 3, the method of the present invention comprises the steps of attaching suitable stabilized electrodes to two separate locoations on the patient's chest wall which have been selected for certain P and QRS vector properties, i.e., contrasting phase properties, contrasting amplitude properties or both. Next, the electrical signals arising from the electrode pair are preprocessed by amplification and filtering. This filtering acts to eliminate aliasing in the A/D conversion by maintaining the signal bandwidth equal to or less than one-half the sampling rate chosen for the A/D conversion process. The amplifier gains are adjusted so that the analog signal is appropriately matched to the A/D converter employed. Next, a subsequent and related filtering stage is imposed, whereby that portion of the QRS energy which is least uniform between channels is filtered out. This filtering may be implemented as an analog filter, and combined with the standard anti-aliasing filter which precede A/D conversion, or may be implemented as digital filters following A/D conversion.

Next, the amplified and filtered "input" and "desired" signals are applied as inputs to an analog-to-digital converter, as illustrated in FIG. 3, and the thus digitized signals are supplied to a computer which has been preprogrammed with the LMS algorithm. The memory of the microprocessor also holds certain control parameters appropriate to processing the digitized surface electrocardiogram signals. For example, the memory of the microprocessor store the number of tap weights assigned to the LMS filter when it is functioning as a finite impulse response or "FIR" filter. For the present application of detecting P-waves in surface ECG traces, the number of tap weights are chosen so that at the particular A/D sampling rate and for the particular bandwidth chosen for the prefiltering, the tap weights will just span the length or duration of the QRS portion of the overall cardiac PQRST complex. As an illustration, if the QRS complex is on the order of 50 milliseconds duration and the A/D converter is sampling the arriving "input" and "desired" signal channels at a 250 Hz rate, there will be approximately 12 to 15 samples taken across the QRS segment. Thus, anywhere from eight to thirty-two tap weights have been found sufficient for the assumed conditions.

The other control parameter which primarily acts to control convergence is the factor, $\mu$. As was explained in my aforereferenced co-pending and co-filed patent application, in the adaptive LMS filter, the weight vector is updated in accordance with the formula, $W_{k+1} = W_k + 2\rho\epsilon_k X_K$. Thus, for appropriate update of the tap weight, the factor, $\mu$, must be judiciously chosen. The appropriate value of mu relates to the magnitudes of the eigenvalues of the correlative matrix of the input signal in a way described by Widrow and Stearns. In general, values which are large on a scale from zero to one cause instability, while values close to zero lead to long convergence times.

In that the software for implementing the LMS algorithm has been explained in detail in the aforereferenced pending patent application, which has been incorporated herein by reference, nothing further need be said relative to it except to say that computer programmers or ordinary skill would be in a position to encode a list of instructions for carrying out the sum of the products computations called for by the LMS algorithm. Hence, it is deemed unnecessary to set out the lines machine code listings herein.

Under some circumstances, a high-frequency oscillation, or ringing, may appear in the "error" channel as part of the QRS residue. This is caused by a combination of the parameter mu, the eigenvalues of the input correlation matrix, and unequalized differences in the frequency distributions of the QRS in the "input" and "desired" leads. This oscillation, if not compensated at the LMS input, may be filtered out of the "error" channel by traditional low pass filtering, leaving the P-wave detachable. Once the QRS noise residue has been reduced, standard thresholding techniques can be used to identify the P-wave artifact and its time of occurrence in the ECG waveform. That is to say, a threshold may be set and if that threshold is exceeded, it is presumed that the signal involved is a P-wave and identification is completed. Rather than merely employing linear thresholding, those skilled in the art of signal processing will recognize that more complex thresholding techniques incorporating a running average and standard deviation techniques can be used as well.

Figure 4:
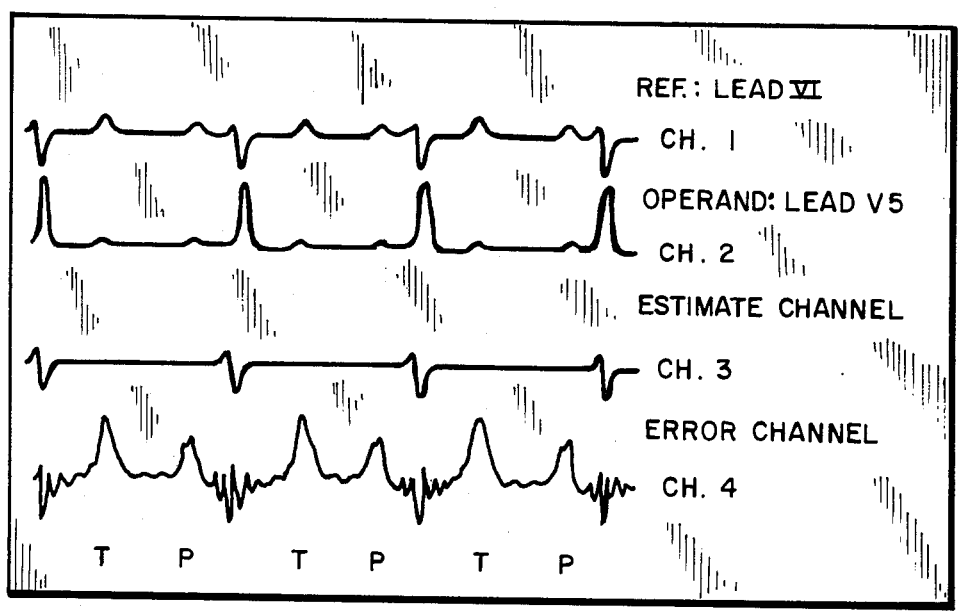
FIG. 4 shows a series of waveforms which illustrate the operation of the present invention.

Referring to FIG. 4, there are shown a series of vertically aligned signal traces showing signal amplitude versus time. The top waveform is a surface ECG signal obtained from electrode $V_1$ in FIG. 2 and the one below it is the ECG signal picked up by surface electrode $V_5$. The next waveform is a trace of the signal developed on the "estimate" channel and the bottommost wave shows the "error" output from the LMS filter operation only amplified by a factor of 4. Comparing waves on channels 1 or 2 with the "error" wave on channel 4 reflects the substantial enhancement of the P-wave and corresponding suppression of the QRS complex. Also, the fact that the QRS component is of a significantly higher frequency component allows subsequent filtering to further enhance the discrimination.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself. In particular, those skilled in the art will realize that the invention can not only be practiced using a programmed digital computer, but also can be implemented using special purpose digital logic devices (hardware).

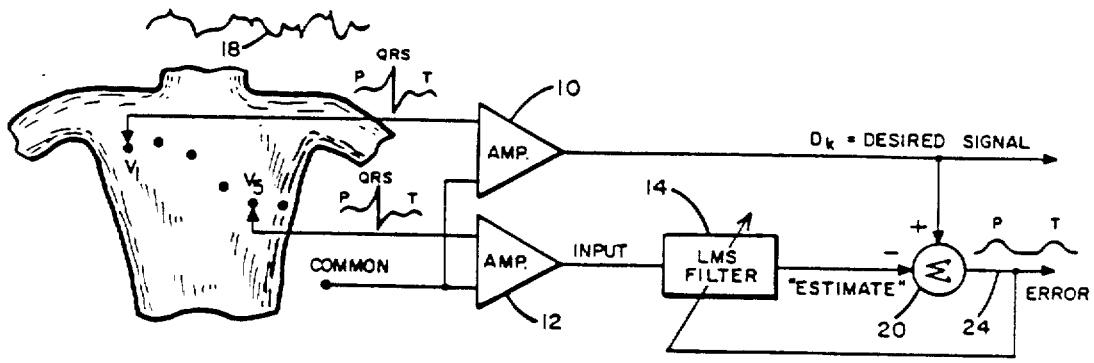

What is claimed is:

1. A system for detecting P-waves in ECG signals obtained from chest contacting surface electrodes, comprising:
   (a) first and second surface electrodes individually coupled to first and second differential amplifying means for obtaining time varying ECG signals from two separate locations on the chest wall of a patient, the output of first differential amplifying means comprising a "reference" waveform;
   (b) adaptive filter means having means for receiving an "input" signal and a "desired" signal and having "error" signal feedback means and "estimate" output means;
   (c) means coupling the output of said first differential amplifying means to said means for receiving a "desired" signal;
   (d) means coupling the output of said second differential amplifying means to said means for receiving an "input" signal;
   (e) summing means connected to receive said "desired" signal and coupled to said "estimate" output means of said adaptive filter means for producing an "error" signal proportional to the difference between said "desired" signal and said "estimate" output means of said adaptive filter means; and
   (f) means coupling said "error" signal feedback means to said adaptive filter means for varying the characteristics of said adaptive filter means whereby the energy content of said "error" signal due to the QRS content of said ECG signals is minimized while the energy content due to the P-wave is enhanced.

2. The system as in claim 1 wherein said adaptive filter means is a least means square filter.

3. The system as in claim 2 wherein said adaptive filter means includes a plurality of variable weighting elements which are updated in accordance with the expression:

$$W_{k+1} = W_k + 2\mu\epsilon_k X_K$$

where k is a time index;
$\epsilon_k$ is said error signal at time k;
$X_k$ is said output signal vector from said second differential amplifier means at time k;
$\mu$ is an adaptation time constant;
$W_k$ is the weight vector value at time k; and
$W_{k+1}$ is the weight vector value at a time later than k following the preceding updating sequence.

4. A method of enhancing the P-wave component of the ECG PQRST complex comprising the steps of:
   (a) attaching at least two electrodes to a patient's skin surface at predetermined locations;
   (b) processing the electrical signals arising from said electrodes by filtering and amplification;
   (c) applying the processed electrical signals to an analog-to-digital converting means for digitizing said electrical signals at a predetermined sampling rate;
   (d) introducing the digitized electrical signals into a digital computer preprogrammed to execute the LMS algorithm, such that the QRS component of the ECG PQRST complex forming the "error" output of said LMS algorithm is substantially reduced while the P-wave component thereof remains substantially unattenuated; and
   (e) comparing said P-wave component in said "error" output to a predetermined reference level.

5. The method as in claim 4 and further including the step of filtering said "error" output of the LMS algorithm to suppress relatively high frequency components therefrom prior to said comparing step.

* * * * *

UNITED STATES PATENT AND TRADEMARK OFFICE
CERTIFICATE OF CORRECTION

PATENT NO. : 4,793,361

DATED : December 27, 1988

INVENTOR(S) : Robert A. DuFault

It is certified that error appears in the above-identified patent and that said Letters Patent is hereby corrected as shown below:

In The Grant Only, the title page should be deleted to appear as per attached title page.

Signed and Sealed this

Fourth Day of July, 1989

Attest:

DONALD J. QUIGG

Attesting Officer

Commissioner of Patents and Trademarks

United States Patent [19]

DuFault

[11] Patent Number: 4,793,361
[45] Date of Patent: Dec. 27, 1988

[54] DUAL CHANNEL P-WAVE DETECTION IN SURFACE ELECTROCARDIOGRAPHS

[75] Inventor: Robert A. DuFault, Roseville, Minn.

[73] Assignee: Cardiac Pacemakers, Inc., St. Paul, Minn.

[21] Appl. No.: 25,731

[22] Filed: Mar. 13, 1987

[51] Int. Cl.$^4$ .................................................. A61B 5/04
[52] U.S. Cl. ..................................................... 128/696
[58] Field of Search ........... 128/696, 704, 705, 419 PG

[56] References Cited

U.S. PATENT DOCUMENTS

| | | | |
|---|---|---|---|
| 4,537,200 | 8/1985 | Widrow | 128/696 |
| 4,543,963 | 10/1985 | Gessman | 128/419 PG |
| 4,557,266 | 12/1985 | Schober | 128/419 PG |

Primary Examiner—Francis J. Jaworski
Assistant Examiner—George Manuel
Attorney, Agent, or Firm—Orrin M. Haugen; Thomas J. Nikolai; Frederick W. Niebuhr

[57] ABSTRACT

A method and apparatus for reliably detecting the P-wave component in a surface electrocardiograph. An adaptive Least Means Square filter is implemented in a programmed computer and the computer receives as its inputs a digitized version of the ECG waves picked up from two discrete locations on a subject's chest wall. The LMS adaptive filter functions to accommodate the energy component of the QRS complex thereby leaving the P-wave as the paramount signal component in the filter's "error" output.

5 Claims, 2 Drawing Sheets